US 8,313,897 B2

(12) United States Patent
Drew

(10) Patent No.: US 8,313,897 B2
(45) Date of Patent: Nov. 20, 2012

(54) METHOD FOR PRESERVING VIRAL PARTICLES

(75) Inventor: Jeffrey Drew, South Kensington (GB)

(73) Assignee: Stabilitech Ltd., London (GB)

( * ) Notice: Subject to any disclaimer, the term of this patent is extended or adjusted under 35 U.S.C. 154(b) by 272 days.

(21) Appl. No.: 12/531,902

(22) PCT Filed: Mar. 19, 2008

(86) PCT No.: PCT/GB2008/000987
§ 371 (c)(1),
(2), (4) Date: Sep. 18, 2009

(87) PCT Pub. No.: WO2008/114021
PCT Pub. Date: Sep. 25, 2008

(65) Prior Publication Data
US 2010/0015177 A1 Jan. 21, 2010

Related U.S. Application Data

(60) Provisional application No. 60/917,220, filed on May 10, 2007.

(30) Foreign Application Priority Data

Mar. 19, 2007 (GB) .................................. 0705245.9

(51) Int. Cl.
*C12Q 1/70* (2006.01)
*A61K 39/02* (2006.01)
(52) U.S. Cl. ..... 435/5; 424/204.1; 424/281.1; 424/93.6; 435/307.1
(58) Field of Classification Search .................. None
See application file for complete search history.

(56) References Cited

U.S. PATENT DOCUMENTS 7,722,884 B2 * 5/2010 Shields et al. ............. 424/209.1
2004/0110267 A1 6/2004 Sundar

FOREIGN PATENT DOCUMENTS

| EP | 1 398 038 A1 | 3/2004 |
|---|---|---|
| WO | WO 99/27071 | 6/1999 |
| WO | WO 2006/085082 | 8/2006 |

OTHER PUBLICATIONS

Han et al., Effect of Molecular Weights of Polyethyleneimine on the Polyplex Formation with Calf Thymus DNA, 2004, Macromolecular Research, vol. 12, No. 3, pp. 276-281.*
Butchaiah and Rao, Freeze-drying of foot and mouth disease virus and its application in inactivated virus vaccine production, 1988, Rev. Sci. Tech. Off. Int. Epiz., vol. 7, No. 2, pp. 347-356.*
Armstrong et al., "Immobilization of Nonviral Vectors During the Freezing Step of Lyophilization," J. Pharm. Sci. 93:2698-2709, 2004.
Carpenter et al., "Separation of Freezing- and Drying-Induced Denaturation of Lyophilized Proteins Using Stress-Specific Stabilization, I. Enzyme Activity and Calorimetric Studies," Arch. Biochem. Biophys. 303:456-464, 1993.
Tan et al., "Freeze-Drying of Fungi: Influence of Composition and Glass Transition Temperature of the Protectant," Cryobiol. 32:60-67, 1995.
International Search Report and Written Opinion from International Application No. PCT/GB2008/000987, dated Jul. 8, 2008 (date of completion of search) and Jul. 23, 2008 (date of mailing).
International Preliminary Report on Patentability from International Application No. PCT/GB2008/000987, dated Mar. 12, 2009 (date of completion of report).

* cited by examiner

*Primary Examiner* — Benjamin P Blumel
(74) *Attorney, Agent, or Firm* — Clark & Elbing LLP

(57) ABSTRACT

A method for preserving viral particles comprises: (i) providing an aqueous solution of one or more sugars, a polyethyleneimine and said viral particles wherein the concentration of polyethyleneimine is 15 μM or less based on the number-average molar mass ($M_n$) of the polyethyleneimine and the sugar concentration or, if more than one sugar is present, total sugar concentration is greater than 0.1 M; and (ii) drying the solution to form an amorphous solid matrix comprising said viral particles.

13 Claims, 6 Drawing Sheets

*P<0.05

Figure 4.1
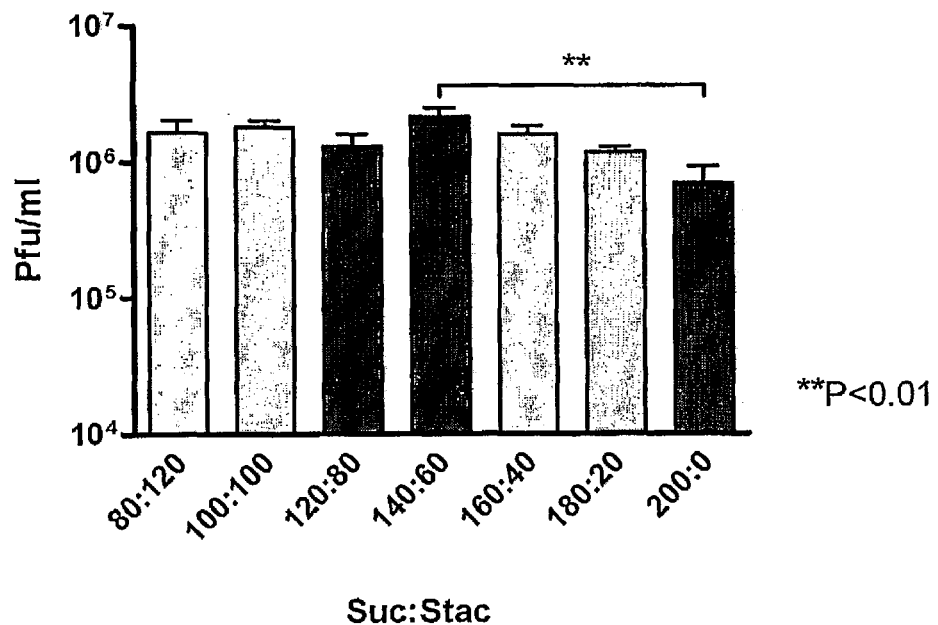
**P<0.01
Figure 4.2
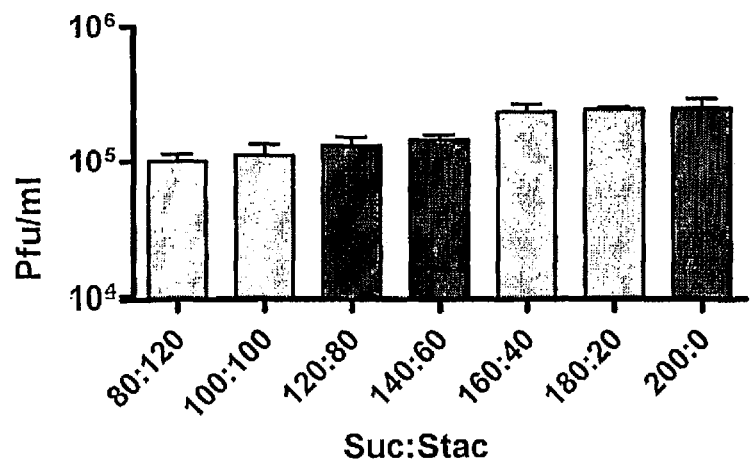

US 8,313,897 B2

METHOD FOR PRESERVING VIRAL PARTICLES

CROSS-REFERENCE TO RELATED APPLICATIONS

This application claims priority under 35 U.S.C. §371 from international application PCT/GB2008/00987, filed Mar. 19, 2008, which claims priority from GB Application No. 0705245.9, filed Mar. 19, 2007, and U.S. Application No. 60/917,220, filed May 10, 2007.

FIELD OF THE INVENTION

The invention relates to methods of preserving viral particles from thermal degradation and desiccation. The invention also relates to products comprising preserved viral particles.

BACKGROUND TO THE INVENTION

Some biological molecules are sufficiently stable that they can be isolated, purified and then stored in solution at room temperature. However, this is not possible for many materials and techniques involving storage at low temperature, addition of stabilisers, freeze-drying, vacuum formation and air-drying have been tried to ensure shelf preservation. Despite the availability of these techniques, some biological materials still show unsatisfactory levels of stability during storage and some techniques lead to added cost and inconvenience. For example, refrigerated transportation and storage is expensive. Further, refrigerated transport is often not available for the transport of medicines such as vaccines in countries in the developing world.

In particular, the stresses of freeze-drying or lyophilisation can be very damaging to some biological materials. Freeze drying of biopharmaceuticals involves freezing solutions or suspensions of thermosensitive biomaterials, followed by primary and secondary drying. The technique is based on sublimation of water at subzero temperature under vacuum without the solution melting. Freeze-drying represents a key step for manufacturing solid protein and vaccine pharmaceuticals. The rate of water vapour diffusion from the frozen biomaterial is very low and therefore the process is time-consuming. Additionally, both the freezing and drying stages introduce stresses that are capable of unfolding or denaturing proteins.

WO-A-2006/0850082 reports a desiccated or preserved product comprising a sugar, a charged material such as a histone protein and a dessication- or thermo-sensitive biological component. The sugar forms an amorphous solid matrix. However, the histone may have immunological consequences if the preserved biological component is administered to a human or animal.

SUMMARY OF THE INVENTION

The present inventor has found that viral preparations mixed with an aqueous solution containing one, two or more sugars and a polyethyleneimine (PEI) are preserved on drying such as on freeze-drying. The addition of one or more sugars to a viral preparation leads to some preservation of viral infectivity and/or immunogenicity. However, the addition of PEI together with one or more sugars surprisingly leads to improved preservation of viral infectivity and/or immunogenicity. A particularly preferred improvement in infectivity and/or immunogenicity is seen at relatively low concentrations of PEI and relatively high concentrations of one or more sugars.

Accordingly, the present invention provides a method for preserving viral particles comprising:
(i) providing an aqueous solution of one or more sugars, a polyethyleneimine and said viral particles wherein the concentration of polyethyleneimine is 15 µM or less based on the number-average molar mass ($M_n$) of the polyethyleneimine and the sugar concentration or, if more than one sugar is present, total sugar concentration is greater than 0.1M; and
(ii) drying the solution to form an amorphous solid matrix comprising said viral particles.

The invention further provides:
a preserved product comprising viral particles, one or more sugars and polyethyleneimine, which product is in the form of an amorphous solid;
an excipient for the preservation of viral particles comprising:
 (a) sucrose, stachyose or raffinose or any combination thereof; and
 (b) polyethyleneimine at a concentration based on $M_n$ of 5 µM or less;
use of the excipient for the preservation of viral particles during and after freeze-drying.
a kit comprising the excipient;
a vaccine comprising the preserved product and optionally an adjuvant;
a method of preparing a vaccine comprising viral particles, the method comprising:
 (a) providing an aqueous solution of one or more sugars, a polyethyleneimine and said viral particles wherein the concentration of polyethyleneimine is 15 µM or less based on the number-average molar mass ($M_n$) of the polyethyleneimine and the sugar concentration or, if more than one sugar is present, total sugar concentration is greater than 0.1M; and
 (b) optionally adding an adjuvant, buffer, antibiotic and/or additive to the admixture; and
 (c) drying the solution to form an amorphous solid matrix comprising said viral particles; and
a dry powder comprising preserved viral particles, obtainable by the method of the invention.

BRIEF DESCRIPTION OF THE FIGURES

FIG. 4.1 shows the effect of the sucrose (Suc):stachyose (Stac) ratio on recovery of freeze-dried HT FMDV-O with varying PEI concentrations. The results show that the addition of Stac increases stability. The results for each PEI concentration were collated. Statistical analysis using a one way ANOVA followed by a Turkey Test showed that a mix containing all Suc achieved significantly lower recovery than one containing a 140:60 by volume Suc:Stac ratio. Error bars show standard error of the mean (n=8).

FIG. 4.2 shows the effect of Suc:Stac ratio on recovery of freeze-dried HT FMDV-O with varying concentrations of histone (His) according to WO-A-2006/0850082. The histone was histone 2A obtained from Boehringer Mannheim. Error bars shown are standard error of the mean (n=6).

FIG. 5 shows the effect of optimisation of the proportions of Suc/Stac/PEI on adenovirus recovery. Plaque forming unit (PFU) formation was assessed following freeze drying for 12 hours and heat treating for 24 hours. The results demonstrate when, using the highest levels of Stac, virus PFU dropped off rapidly. With no Stac present, PFU was dramatically reduced. When freeze dried with only PBS, there were no PFU. Lower dilutions of PEI also appeared to enhance virus recovery.

FIG. 6 shows adenovirus recovery in PEI and sugar. PEI and sugar excipient were optimised and compared to 3 controls; sugars only, PBS and the original titre (before freeze drying). Freeze drying with PBS only showed no thermoprotection. Sugars only showed some viral activity, however, greater activity was seen using PEI together with sugar in the excipient. Error bars shown are standard error of the mean (n=2).

FIG. 7 shows that an excipient containing Suc (1.5M)/Stac (0.125M) with PEI at a concentration of 0.02 nM appears optimal and demonstrates improved recovery of adenovirus over just a Suc Stac solution alone. PEI as the sole excipient showed little to no protection during freeze drying.

FIG. 8 shows the results of an experiment designed to compare two different PEIs on adenoviral recovery. The high molecular weight PEI was effective at a much lower concentration than the low molecular weight PEI. PBS alone showed no virus recovery. Again optimal PEI/sugar concentrations show improved recovery over sugars alone.

FIG. 9 show a comparison between diluting PEI in water ("PEIW") and diluting PEI in PBS ("PEIP"). The results showed higher adenovirus titres when PEI is diluted in PBS as opposed to water. When used as excipients on their own both PBS and distilled water showed a very low level of adenovirus recovery.

DETAILED DESCRIPTION OF THE INVENTION

Summary

The present invention relates to the preservation of viral particles by contacting the viral particles with a preservation mixture. The preservation mixture is an aqueous solution of PEI and one, two or more sugars. Low concentrations of PEI and relatively high concentrations of sugar are used. The solution in which the viral particles are present is then dried to form an amorphous solid matrix comprising the viral particles.

The invention thus enables virus structure and function to be preserved during the drying step. Virus activity following drying can thus be maintained. The preserved viral particles demonstrate improved thermal and desiccation resistance allowing extension of shelf life, ease of storage and transport and obviating the need for a cold chain for distribution. The invention can thus provide protection as a cryoprotectant (protection against freeze damage), lyoprotectant (protection against desiccation) and/or a thermoprotectant (protection against temperatures higher or lower than 4° C.).

Viral Particles

Typically, a whole virus or virion consists of nucleic acid surrounded by a protective protein coat or capsid. Viral nucleic acid may comprise DNA, RNA, single stranded RNA, double-stranded RNA, double stranded DNA, mRNA or any combination thereof.

The capsid is made up of subunits. Many viral capsids are made up of subunits which may have either icosahedral or helical symmetry. Some types of virus also include viral structures such as a nucleocapsid, extra structures such as protein tails and complex outer walls, and complex structures such as an icosahedral head bound to a helical tail. The capsid may also be surrounded by an envelope. The envelope is composed of lipoprotein bilayer and may contain material from the membrane of a host cell as well as that of viral origin. For example, the envelope may contain cell-derived lipids and virus-derived proteins. Viruses may also contain glycoprotein spikes.

The viral particles used in the present invention may be whole viruses such as live viruses, killed viruses, live attenuated viruses, inactivated viruses such as chemically inactivated viruses or virulent or non-virulent viruses. A live virus is capable of infecting and being reproduced by the viral host. A killed virus is inactivated and is unable to infect the viral host. The particles may be virus-like particles (VLPs) or nucleocapsids.

The viral particle may be or may be derived from a dsDNA virus, a ssDNA virus, a dsRNA virus, a (+)ssRNA virus, a (−)ssRNA virus, a ssRNA-RT virus or a dsDNA-RT virus. As an example but not intended to be limiting, the viral particle can be or can be derived from a virus of the following families:

- adenoviridae such as human adenovirus A, B, C, D, E or F including human Ad5, Ad2, Ad6, Ad24 serotypes;
- caliciviridae such as the norwalk virus;
- coronaviridae such as human coronavirus 299E or OC43 and SARS-coronavirus;
- filoviridae such as ebola virus;
- flaviviridae such as yellow fever virus, west nile virus, dengue virus, hepatitis C virus;
- hepadnaviridae such as hepatitis B virus;
- herpesviridae such as herpes simplexvirus, human herpesvirus 1, 3, 4, 5 or 6;
- orthomyxoviridae such as influenzavirus A, B, C including but not limited to influenza A virus serotypes H1N1, H2N2, H3N2, H5N1, H7N7, H1N2, H9H2, H7N2, H7N3 and N10N7;
- papillomaviridae such as human papilloma virus;
- paramyxoviridae such as human parainfluenza virus 1, measles virus and mumps virus;
- parvoviridae such as adeno-associated virus;
- picornaviridae such as human poliovirus, foot and mouth disease virus (including serotypes O, A, C, SAT-1, SAT-2, SAT-3 and Asia-1);
- poxyiridae such as vaccinia virus, variola virus and avian poxvirus (fowlpox);
- reoviridae such as bluetongue virus group;
- retroviridae such as lentivirus including human immunodeficiency virus 1 and 2; and
- togaviridae such as rubella virus.

In a preferred embodiment, the viral particle can be or can be derived from an adenoviridae, orthomyxoviridae, parvoviridae, picornaviridae or poxyiridae virus. In a particularly preferred embodiment, the viral particle can be or can be derived from an adenovirus, vaccinia virus, influenza virus, or foot and mouth disease virus.

Figure 1:
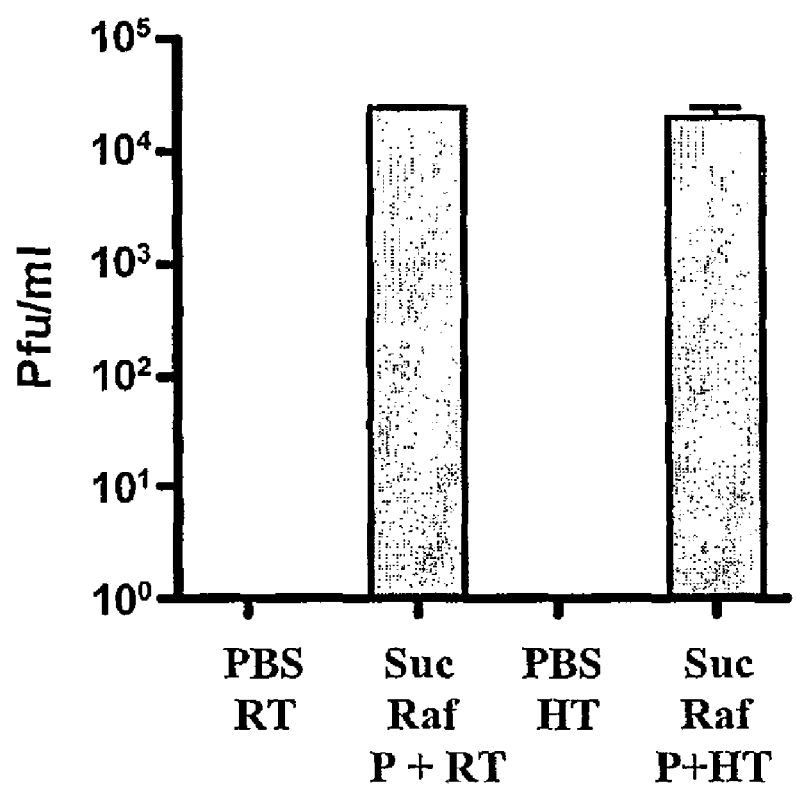
FIG. 1 shows the effect of an excipient composed of PEI, sucrose (Suc) and raffinose (Raf) on Foot and Mouth Disease Virus (FMDV-A) recovery following freeze-drying and either incubation for 24 hours at room temperature (RT) or heat treatment for 48 at 37° C. (HT). The results also show that phosphate buffered saline (PBS) offers no protection during freeze-drying (FD). Error bars shown are standard error of the mean (n=2).

Virus-like particles (VLPs) include viral proteins derived from the structural proteins of a virus, but lack viral nucleic acid. When overexpressed, these viral structural proteins spontaneously self-assemble into particles. VLPs are replication incompetent. In some embodiments, the VLPs are viral proteins embedded within a lipid bilayer. Examples of VLPs includes phage-derived VLPs, human papillomavirus (HPV) L1 major capsid protein VLPs, Norwalk virus capsid protein VLPs and VLPs assembled from influenza virus structural proteins such as M1 protein, HA hemagglutinin protein and N1 neuraminidase protein.

Viral particles can be prepared using standard techniques well known to those skilled in the art. For example, a virus may be prepared by infecting cultured host cells with the virus strain that is to be used, allowing infection to progress such that the virus replicates in the cultured cells and can be released by standard methods known in the art for harvesting and purifying viruses.

Preservation Mixture

The preservation mixture of the present invention comprises an aqueous solution of one or more sugars and a polyethyleneimine (PEI). Any suitable aqueous solution may be used. The solution may be buffered. The solution may be a HEPES solution, phosphate-buffered saline (PBS) or pure water.

Sugars suitable for use in the present invention include reducing sugars such as glucose, fructose, glyceraldehydes, lactose, arabinose and maltose; and non-reducing sugars such as sucrose. The sugar may be a monosaccharide, disaccharide, trisaccharide, or other oligosaccharides. The term "sugar" includes sugar alcohols.

Monosaccharides such as galactose, raffinose and mannose; dissaccharides such as lactose and maltose; and tetrasaccharides such as stachyose are envisaged. Trehalose, umbelliferose, verbascose, isomaltose, cellobiose, maltulose, turanose, melezitose and melibiose are also suitable for use in the present invention. A suitable sugar alcohol is mannitol.

Preferably, the aqueous solution of one, two or more sugars is a solution of sucrose, raffinose or stachyose. In particular, sucrose is a disaccharide of glucose and fructose; raffinose is a trisaccharide composed of galactose, fructose and glucose; and stachyose is a tetrasaccharide consisting of two Dα-galactose units, one Dα-glucose unit and one Dβ-fructose unit sequentially linked. A combination of sucrose and raffinose, or of sucrose and stachyose may be employed.

Preservation of viral infectivity or immunogenicity is particularly effective when at least two sugars are used in the preservation mixture of the present invention. Therefore, the solution of one or more sugars comprises a solution of at least 2, at least 3, at least 4 or at least 5 sugars. Combinations of 2, 3, 4, 5, 6, 7, 8, 9, 10, etc sugars are envisaged. Preferably, the solution of two or more sugars comprises sucrose and raffinose, or sucrose and stachyose.

PEI is an aliphatic polyamine characterised by the repeating chemical units denoted as —(CH$_2$—CH$_2$—NH)—. Reference to PEI herein includes a polyethyleneimine homopolymer or copolymer. The polyethyleneimine copolymer may be a random or block copolymer. For example, PEI may consist of a copolymer of polyethyleneimine and another polymer such as polyethylene glycol (PEG). The polyethyleneimine may be linear or branched.

Reference to PEI also includes derivatised forms of a polyethyleneimine. A polyethyleneimine contains nitrogen atoms at various positions. Nitrogen atoms are present in terminal amino groups, e.g. R—NH$_2$, and in internal groups such as groups interrupting an alkyl or alkylene group within the polymer structure, e.g. R—N(H)—R', and at the intersection of a polymer branch, e.g. R—N(—R')-R" wherein R, R' and R" may be alkylene groups for example. Alkyl or aryl groups may be linked to the nitrogen centres in addition to or instead of hydrogen atoms. Such alkyl and aryl groups may be substituted or unsubstituted. An alkyl group would be typically a $C_1$-$C_4$ alkyl group, e.g. methyl, ethyl, propyl, isopropyl, butyl, sec.butyl or tert.butyl. The aryl group is typically phenyl.

The PEI may be a polyethyleneimine that has been covalently linked to a variety of other polymers such as polyethylene glycol. Other modified versions of PEI have been generated and some are available commercially: branched PEI 25 kDa, jetPEI®, LMW-PEI 5.4 kDa, Pseudodendrimeric PEI, PEI-SS-PEI, PEI-SS-PEG, PEI-g-PEG, PEG-co-PEI, PEG-g-PEI, PEI-co-L lactamide-co-succinamide, PEI-co-N-(2-hydroxyethyl-ethylene imine), PEI-co-N-(2-hydroxypropyl) methacrylamide, PEI-g-PCL-block-PEG, PEI-SS-PHMPA, PEI-g-dextran 10 000 and PEI-g-transferrin-PEG, Pluronic85®/Pluronic123®-g-PEI.

PEI is available in a broad range of number-average molar masses ($M_n$) for example between 300 Da and 800 kDa. Preferably, the number-average molar mass is between 300 and 2000 Da, between 500 and 1500 Da, between 1000 and 1500 Da, between 10 and 100 kDa, between 20 and 100 kDa, between 30 and 100 kDa, between 40 and 100 kDa, between 50 and 100 kDa, between 60 and 100 kDa, between 50 and 70 kDa or between 55 and 65 kDa. A relatively high $M_n$ PEI of approximately 60 kDa or a relatively low $M_n$ of 1200 Da is suitable.

Preferably, the weight-average molar mass ($M_w$) of PEI is between 500 Da and 1000 kDa. Most preferably, the $M_w$ of PEI is between 500 and 2000 Da, between 1000 Da and 1500 Da, or between 1 and 1000 kDa, between 100 and 1000 kDa, between 250 and 1000 kDa, between 500 and 1000 kDa, between 600 and 1000 kDa, between 750 and 1000 kDa, between 600 and 800 kDa, between 700 and 800 kDa. A relatively high $M_w$ of approximately 750 kDa or a relatively low $M_w$ of approximately 1300 Da is suitable.

The weight-average molar mass ($M_w$) and number-average molar mass ($M_n$) of PEI can be determined by methods well known to those skilled in the art. For example, $M_w$ may be determined by light scattering, small angle neutron scattering (SANS), X-ray scattering or sedimentation velocity. $M_n$ may be determined for example by gel permeation chromatography, viscometry (Mark-Houwink equation) and colligative methods such as vapour pressure osometry or end-group titration.

Various forms of PEI are available commercially (e.g. Sigma, Aldrich). For example, a branched, relatively high molecular weight form of PEI used herein with an $M_n$ of approximately 60 kDa and a $M_w$ of approximately 750 kDa is available commercially (Sigma P3143). This PEI can be represented by the following formula:

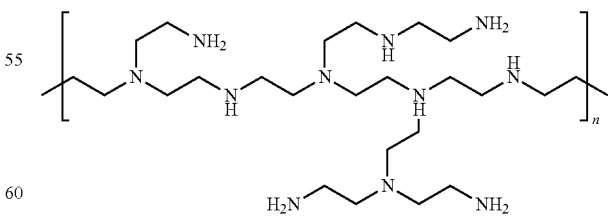

A relatively low molecular weight form of PEI used herein is also available commercially (e.g. Aldrich 482595) which has a $M_w$ of 1300 Da and $M_n$ of 1200 Da.

In the present invention, a preservation mixture comprising an aqueous solution of PEI and one, two or more sugars is provided. Typically, the viral particles are admixed with the preservation mixture to provide the aqueous solution for drying.

The concentration of sugar in the aqueous solution for drying is greater than 0.1M. Preferably, the concentration of the sugar in the aqueous solution for drying or, if more than one sugar is present, the total concentration of sugar in the aqueous solution for drying, is at least 0.2M, 0.3M, 0.4M, 0.5M, 0.6M, 0.75M, 0.9M, 1M or 2M up to saturation e.g. saturation at room temperature or up to 3M, 2.5M or 2M. The sugar concentration or the total concentration if more than one sugar is present may be from 0.5 to 2M. When more than one sugar is present, each sugar may be present at a concentration of from 0.2M, 0.3M, 0.4M, 0.5M, 0.6M, 0.75M, 0.9M, 1M or 2M up to saturation e.g. saturation at room temperature or up to 3M, 2.5M or 2M.

The concentration of PEI in the aqueous solution for drying is generally in the range of 15 μM or less based on $M_n$. The PEI concentration may be 10 μM or less based on $M_w$. Such concentrations of PEI are particularly effective at preserving viral infectivity or immunogenicity.

In a preferred embodiment of the invention, the PEI is provided at a concentration based on $M_n$ of less than 5 μM, less than 500 nM, less than 100 nM, less than 40 nM, less than 25 nM, less than 10 nM, less than 5 nM, less than 1 nM, less than 0.5 nM, less than 0.25 nM, less than 0.1 nM, less than 0.075 nM, less than 0.05 nM, less than 0.025 Nm or less than 0.0025 nM. Typically the PEI concentration based on $M_n$ is 0.0025 nM or more, 0.025 nM or more, or 0.1 nM or more. A suitable PEI concentration range based on $M_n$ is between 0.0025 nM and 5 μM, or between 0.025 and 200 nM.

Preferably, the PEI concentration based on $M_w$ is less than 5 μM, less than 1 μM, less than 0.1 μM, less than 0.1 μM, less than 5 nM, less than 4 nM, less than 2 nM, less than 1 nM, less than 0.5 nM, less than 0.25 nM, less than 0.1 nM, less than 0.05 nM, less than 0.02 nM, less than 0.002 nM or less than 0.1 nM. Typically the PEI concentration based on $M_w$ is 0.00001 nM or more, 0.001 nM or more or 0.01 nM or more. A suitable PEI concentration range based on $M_w$ is between 0.00001 and 20 nM, between 0.0001 and 20 nM or between 0.0001 and 5 nM.

Typically, it is found that relatively high molecular weight PEI is effective at lower concentrations than relatively low molecular weight PEI. Thus:

Where a relatively high $M_w$ PEI is used, for example in the range of 20 to 1000 kDa, a concentration of PEI of between 0.001 and 5 nM based on $M_w$ is preferred. Where a relatively low $M_w$ PEI is used, for example in the range of 300 Da to 10 kDa, a concentration of PEI of between 0.0001 and 10 μM is preferred.

Where a relatively high $M_n$ PEI is used, for example in the range of 20 to 1000 kDa, the concentration of PEI based on $M_n$ is preferably between 0.001 and 100 nM. Where a relatively low $M_n$ is used, for example in the range of 1 Da to 10 kDa, a concentration of PEI of between 0.0001 and 10 μM is used.

In an embodiment, the preservation mixture initially contacted with the viral particles comprises PEI at a concentration based on $M_n$ of less than 2 μM and a solution of one or more sugars at a concentration of at least 0.1M, at least 0.2M, at least 0.3M, at least 0.4M, at least 0.5M, at least 0.75M, at least 0.9M, at least 1M, or at least 2M.

When the solution of one or more sugars comprises two or more sugars, the most effective concentration of PEI will be dependent on the particular type of sugar used in the preservation mixture. For example, when one of the two or more sugars is sucrose and the other is stachyose, PEI at a concentration based on $M_n$ of less than 2 μM, in particular at a concentration between 0.025 nM and 2 μM, is effective at preservation. In a preferred embodiment, the method of the invention involves admixing the viral particles with an aqueous solution of (i) one or more sugars wherein one of these sugars is sucrose and the other is stachyose and (ii) PEI at a concentration based on $M_n$ of less than 2 μM.

When the aqueous solution of two or more sugars comprises an aqueous solution of sucrose and raffinose the preferred concentration of PEI is found to be less than 2 μM, or in the range between 0.0025 nM and 2 μM. Therefore in a further embodiment, the method of the invention involves admixing the viral particles with an aqueous solution of (i) sucrose and raffinose and (ii) PEI at a concentration between 0.0025 nM and 2 μM. Preferably, when a relatively high molecular weight PEI is used, for example between 10 and 100 kDa based on $M_n$, the concentration of PEI based on $M_n$ is between 0.1 and 100 nM.

Whilst using a combination of two sugars in the preservation mixture, the present inventors investigated the effect of different molar concentration ratios of these sugars on the preservation of the viral particle. Specific molar concentration ratios of one sugar to another were particularly effective but the exact ratio depended on the types of sugar used. Therefore in one embodiment of the invention in which one of the two or more sugars comprises sucrose, the concentration of sucrose relative to the other sugar is at a ratio of molar concentrations of between 3:7 and 9:1, preferably at a ratio of at least 4:6, at least 50:50, at least 6:4, at least 7:3, at least 8:2 or at least 9:1. In the case of sucrose and stachyose, a ratio of molar concentrations of sucrose:stachyose of at least 3:7, at least 4:6, at least 50:50, at least 6:4, at least 7:3, at least 3:1, at least 8:2 or at least 9:1 demonstrated particularly effective preservation. Preferably, the solution of two or more sugars comprises a solution of sucrose and stachyose at a ratio of molar concentrations of between 50:50 and 8:2.

In a further embodiment, the preservation mixture of the present invention comprises an aqueous solution of (i) two or more sugars in which one of the sugars is sucrose and the concentration of sucrose relative to the other sugar is at a ratio of molar concentrations between 3:7 and 9:1 and (ii) PEI at a concentration of less than 100 nM or at a concentration based on $M_n$ between 0.025 and 100 nM.

Preservation

The preservation techniques of the present invention are particularly suited to preservation against desiccation and freezing of viral particles and thermal challenge. Preservation of viral particles is achieved by drying viral particles admixed with the preservation mixture of the present invention. On drying, an amorphous solid is formed. By "amorphous" is meant non-structured and having no observable regular or repeated organization of molecules (i.e. non-crystalline).

Typically, drying is achieved by freeze-drying, snap-freezing, vacuum drying or spray-drying. Freeze-drying is preferred. By removing the water from the material and sealing the material in a vial, the material can be easily stored, shipped and later reconstituted to its original form.

Freeze-drying is a dehydration process typically used to preserve perishable material or make the material more convenient for transport. Freeze-drying represents a key step for manufacturing solid protein and vaccine pharmaceuticals. However, biological materials are subject to both freezing and drying stresses during the procedure, which are capable of unfolding or denaturing proteins. Furthermore, the rate of water vapour diffusion from the frozen biological material is very low and therefore the process is time-consuming. The preservation technique of the present invention enables biological materials to be protected against the desiccation and/or thermal stresses of the freeze-drying procedure.

There are three main stages to this technique namely freezing, primary drying and secondary drying. Freezing is typically performed using a freeze-drying machine. In this step, it is important to cool the biological material below its eutectic point, the lowest temperature at which the solid and liquid phase of the material can coexist. This ensures that sublimation rather than melting will occur in the following steps. Alternatively, amorphous materials do not have a eutectic point, but do have a critical point, below which the product must be maintained to prevent melt-back or collapse during primary and secondary drying.

During primary drying the pressure is lowered and enough heat supplied to the material for the water to sublimate. The amount of heat necessary can be calculated using the sublimating molecules' latent heat of sublimation. About 95% of the water in the material is sublimated at this stage. Primary drying may be slow as too much heat could degrade or alter the structure of the biological material. In order to control the pressure, a partial vacuum is applied which speeds sublimation. A cold condenser chamber and/or condenser plates provide a surface(s) for the water vapour to re-solidify on.

In the secondary drying process, water molecules adsorbed during the freezing process are sublimated. The temperature is raised higher than in the primary drying phase to break any physico-chemical interactions that have formed between the water molecules and the frozen biological material. Typically, the pressure is also lowered to encourage sublimation. After completion of the freeze-drying process, the vacuum is usually broken with an inert gas, such as nitrogen, before the material is sealed.

In one embodiment, drying is achieved by freezing the mixture, such as by snap freezing. The term "snap freezing" means a virtually instantaneous freezing as is achieved, for example, by immersing a product in liquid nitrogen. In some embodiments it refers to a freezing step, which takes less than 1 to 2 seconds to complete.

In certain embodiments, drying is carried out using vacuum desiccation at around 1300 Pa. However vacuum desiccation is not essential to the invention and in other embodiments, the preservation mixture contacted with the viral particle is spun (i.e. rotary desiccation) or freeze-dried (as further described below). Advantageously, the method of the invention further comprises subjecting the preservation mixture containing the viral particle to a vacuum. Conveniently, the vacuum is applied at a pressure of 20,000 Pa or less, preferably 10,000 Pa or less. Advantageously, the vacuum is applied for a period of at least 10 hours, preferably 16 hours or more. As known to those skilled in the art, the period of vacuum application will depend on the size of the sample, the machinery used and other parameters.

In another embodiment, drying is achieved by spray-drying the viral particles admixed with the preservation mixture of the invention. This technique is well known to those skilled in the art and involves a method of drying a liquid feed through a hot gas e.g. air, oxygen-free gas or nitrogen. The liquid feed is atomized into a spray of droplets. The droplets are then dried by contact with the hot gas in a drying chamber.

Once mixed with the preservation mixture, the samples can be dried to various residual moisture contents to offer long term preservation at greater than refrigeration temperatures e.g. within the range from about 4° C. to about 45° C., or lower than refrigeration temperatures e.g. within the range from about 0 to −70° C. or below.

Using the method of the invention, the admixture of viral particles and preservation mixture is dried to form an amorphous solid matrix. In one embodiment of the invention, the amorphous solid is obtained in a dry powder form. The amorphous solid may take the form of free-flowing particles.

However, in a further embodiment of the method of the invention, the admixture comprising viral particles is dried onto a solid support. The solid support may comprise a bead, test tube, matrix, plastic support, microtiter dish, microchip (for example, silicon, silicon-glass or gold chip), or membrane. In another embodiment, there is provided a solid support onto which a viral particle preserved according to the methods of the present invention is dried or attached.

The present invention provides a kit comprising an excipient comprising an aqueous solution of (i) one or more sugars and (ii) PEI. Preferably the kit comprises further excipients, carriers or diluents suitable for veterinary or pharmaceutical purposes. Instructions for administration may also be provided. The kit may also comprise auxiliary substances, such as adjuvants, setting or emulsifying agents, pH buffer agents, gelling or viscosity enhancing additives or colours, suitable for delivery of the preserved viral particles of the invention into a patient or target cell.

Preservation in relation to viral particles refers to resistance of the viral particle to physical degradation and/or loss of biological activity such as nucleic acid or protein degradation, loss of transduction efficiency, loss of viral infectivity, loss of immunogenicity, loss of virus titre or loss of vaccine potency, under exposure to conditions of desiccation, freezing, temperatures below 0° C., below −5° C., below −10° C., below −15° C., below −20° C. or below −25° C., freeze-drying, room temperature, temperatures above −10° C., above −5° C., above 0° C., above 5° C., above 10° C., above 15° C., above 20° C., above 25° C. or above 30° C. Preferably, preservation according to the present invention comprises cryoprotection (protection against freeze damage), lyoprotection (protection against desiccation) and/or thermoprotection (protection against temperatures higher or lower than 4° C.).

Measuring Viral Particle Preservation

The preservation of viral particles in accordance with the present invention can be measured by the assessment of parameters such as viral infectivity, immunogenicity, transfection rates, virus titre and host cell response. Such techniques are well known to those skilled in the art.

Methods of assaying for viral infectivity and/or immunogenicity are well known to those skilled in the art and include but are not limited to growth of a virus in a cell culture, detection of virus-specific antibody in blood, ability to elicit T and/or B cell responses, detection of viral antigens, detection of virus encoded DNA or RNA, or observation of virus particles using a microscope.

Further, the presence of a virus gives rise to morphological changes in the host cell, which can be measured to give an indication of viral activity. Detectable changes such as these in the host cell due to viral infection are known as cytopathic effect. Cytopathic effects may consist of cell rounding, disorientation, swelling or shrinking, death and detachment from the surface. Many viruses induce apoptosis (programmed cell death) in infected cells, measurable by techniques such as the TUNEL (Terminal uridine deoxynucleotidyl transferase dUTP nick end labelling) assay and other techniques well known to those skilled in the art.

Viruses may also affect the regulation of expression of the host cell genes and these genes can be analysed to give an indication of whether viral activity is present or not. Such techniques may involve the addition of reagents to the cell culture to complete an enzymatic or chemical reaction with a viral expression product. Furthermore, the viral genome may be modified in order to enhance detection of viral infectivity. For example, the viral genome may be genetically modified to express a marker that can be readily detected by phase contrast microscopy, fluorescence microscopy or by radioimaging. The marker may be an expressed fluorescent protein such as GFP (Green Fluorescent Protein) or an expressed enzyme that may be involved in a colourimetric or radiolabelling reaction. The marker could also be a gene product that interrupts or inhibits a particular function of the cells being tested.

An assay for plaque-forming units can be used to measure viral infectivity and to indicate viral titre. In this assay, suitable host cells are grown on a flat surface until they form a monolayer of cells covering a plastic bottle or dish. The selection of a particular host cell will depend on the type of virus. Examples of suitable host cells include but are not limited to CHO, BHK, MDCK, 10T1/2, WEHI cells, COS, BSC 1, BSC 40, BMT 10, VERO, W138, MRC5, A549, HT1080, 293, B-50, 3T3, NIH3T3, HepG2, Saos-2, Huh7, HEK293 and HeLa cells. The monolayer of host cells is then infected with the viral particles. The liquid medium is replaced with a semi-solid one so that any virus particles produced, as the result of an infection cannot move far from the site of their production. A plaque is produced when a virus particle infects a cell, replicates, and then kills that cell. A plaque refers to an area of cells in the monolayer which display a cytopathic effect, e.g. appearing round and darker than other cells under the microscope, or as white spots when visualized by eye; the plaque center may lack cells due to virus-induced lysis. The newly replicated virus infects surrounding cells and they too are killed. This process may be repeated several times. The cells are then stained with a dye such as methylene blue, which stains only living cells. The dead cells in the plaque do not stain and appear as unstained areas on a coloured background.

Each plaque is the result of infection of one cell by one virus followed by replication and spreading of that virus. However, viruses that do not kill cells may not produce plaques. A plaque refers to an area of cells in a monolayer which display a cytopathic effect, e.g. appearing round and darker than other cells under the microscope, or as white spots when visualized by eye; the plaque center may lack cells due to virus-induced lysis. An indication of viral titre is given by measuring "plaque-forming units" (PFU). PFU refers to a virus or group of viruses, which cause a plaque. For example: if a viral stock solution has 1000 pfu/ml, it means that every ml of this stock has 1000 virus particles which can form plaques. Levels of viral infectivity can be measured in a sample of biological material preserved according to the present invention and compared to control samples such as freshly harvested virus or samples subjected to desiccation and/or thermal variation without addition of the preservation mixture of the present invention.

Typically, the viral titre following preservation according to the present invention and incubation of the resulting product at 37° C. for 5 days is at least 10%, at least 20%, at least 30%, at least 40%, at least 50%, at least 60%, at least 70%, at least 80% or at least 90% of the titre of the virus prior to such incubation or, indeed prior to preservation according to the present invention and such incubation.

Some types of viral particles of the invention, such as viral proteins, VLPs, or some inactivated viruses do not have the ability to form plaques in the plaque assay. In this case, preservation can be measured by other methods such as methods for determining immunogenicity which are well known to those skilled in the art. For example, in vivo and in vitro assays for measuring antibody or cell-mediated host immune responses are known in the art and suitable for use in the present invention. For example, an antibody based immune response may be measured by comparing the amount, avidity and isotype distribution of serum antibodies in an animal model, before and after immunization using the preserved viral particle of the invention.

Uses of the Preserved Viral Particles of the Invention

Vaccines

The preserved viral particles of the present invention may find use as a vaccine. For example, preserved viral particles such as whole killed virus, live attenuated virus, chemically inactivated virus, VLPs or live viral vectors are suitable for use as a vaccine. As a vaccine the preserved viral particles of the invention may be used as antigens or to encode antigens such as viral proteins for the treatment or prevention of a number of conditions including but not limited to viral infection, sequelae of viral infection including but not limited to viral-induced toxicity, cancer and allergies. Such antigens contain one or more epitopes that will stimulate a host's immune system to generate a humoral and/or cellular antigen-specific response.

The preserved vaccine of the invention may be used to treat infection by viruses such as human papilloma viruses (HPV), HIV, HSV2/HSV1, influenza virus (types A, B and C), para influenza virus, polio virus, RSV virus, rhinoviruses, rotaviruses, hepaptitis A virus, norwalk virus, enteroviruses, astroviruses, measles virus, mumps virus, varicella-zoster virus, cytomegalovirus, epstein-barr virus, adenoviruses, rubella virus, human T-cell lymphoma type I virus (HTLV-I), hepatitis B virus (HBV), hepatitis C virus (HCV), hepatitis D virus, poxvirus and vaccinia virus. The vaccine may further be used to provide a suitable immune response against numerous veterinary diseases, such as foot and mouth disease (including serotypes O, A, C, SAT-1, SAT-2, SAT-3 and Asia-1), coronavirus, bluetongue, feline leukaemia virus, avian influenza, hendra and nipah virus, pestivirus, canine parvovirus and bovine viral diarrhoea virus. In one embodiment, the vaccine is a subunit, conjugate or multivalent vaccine. For example, the preserved vaccine of the invention may be used to treat infection by two or more different types of virus such as measles, mumps and rubella (e.g. MMR vaccine).

The vaccine compositions of the present invention comprise viral particles admixed with the preservation mixture of the invention containing one or more sugars and PEI. The vaccine composition may further comprise appropriate buffers and additives such as antibiotics, adjuvants or other molecules that enhance presentation of vaccine antigens to specific cells of the immune system.

A variety of adjuvants well known in the art can be used in order to increase potency of the vaccine and/or modulate humoral and cellular immune responses. Suitable adjuvants include, but are not limited to, oil-in-water emulsion-containing adjuvants or water in oil adjuvants, such as mineral oil, aluminium based adjuvants, squalene/phosphate based adjuvants, Complete/Incomplete Freunds Adjuvant, cytokines and any other substances that act as immunostimulating agents to enhance the effectiveness of the vaccine.

The vaccine composition of the present invention can be in a freeze-dried (lyophilised) form in order to provide for appropriate storage and maximize the shelf-life of the preparation. This will allow for stock piling of vaccine for prolonged periods of time and help maintain immunogenicity, potency and efficacy. The preservation mixture of the present invention is particularly suited to preserve viral substances against desiccation and thermal stresses encountered during freeze-drying/lyophilisation protocols. Therefore, the preservation mixture is suitable for adding to the virus or viral particle soon after harvesting and before subjection of the sample to the freeze-drying procedure.

To measure the preservation of a vaccine prepared in accordance with the present invention, the potency of the vaccine can be measured using techniques well known to those skilled in the art. For example, the generation of a cellular or humoral immune response can be tested in an appropriate animal model by monitoring the generation of antibodies or immune cell responses to the vaccine. The ability of vaccine samples prepared in accordance with the method of the present invention to trigger an immune response may be compared with vaccines not subjected to the same preservation technique.

Viral Vectors

A virus or viral vector preserved according to the method of the present invention can be used to transfer a heterologous gene or other nucleic acid sequence to target cells. Suitably, the heterologous sequence (i.e. transgene) encodes a protein or gene product which is capable of being expressed in the target cell. Suitable transgenes include desirable reporter genes, therapeutic genes and genes encoding immunogenic polypeptides (for use as vaccines). Gene therapy, an approach for treatment or prevention of diseases associated with defective gene expression, involves the insertion of a therapeutic gene into cells, followed by expression and production of the required proteins. This approach enables replacement of damaged genes or inhibition of expression of undesired genes. In particular, the preserved virus or viral vector may be used in gene therapy to transfer a therapeutic transgene or gene encoding immunogenic polypeptides to a patient.

In a preferred embodiment, the preserved viral particle is a live viral vector. By "live viral vector" is meant a live viral vector that is non-pathogenic or of low pathogenicity for the target species and in which has been inserted one or more genes encoding antigens that stimulate an immune response protective against other viruses or microorganisms, a reporter gene or a therapeutic protein. In particular, nucleic acid is introduced into the viral vector in such a way that it is still able to replicate thereby expressing a polypeptide encoded by the inserted nucleic acid sequence and in the case of a vaccine, eliciting an immune response in the infected host animal. In one embodiment, the live viral vector is an attenuated live viral vector i.e. is modified to be less virulent (disease-causing) than wildtype virus.

The basis of using recombinant viruses as potential vaccines involves the incorporation of specific genes from a pathogenic organism into the genome of a nonpathogenic or attenuated virus. The recombinant virus can then infect specific eukaryotic cells either in vivo or in vitro, and cause them to express the recombinant protein.

Live viral vector vaccines derived by the insertion of genes encoding sequences from disease organisms may be preferred over live attenuated vaccines, inactivated vaccines, subunit or DNA approaches. One of the most important safety features of live viral vectors is that the recipients may be immunized against specific antigens from pathogenic organisms without exposure to the disease agent itself. Safety is further regulated by the selection of a viral vector that is either attenuated for the host or unable to replicate in the host although still able to express the heterologous antigen of interest. A vaccine strain that has a history of safety in the target species offers an additional safety feature. Several systems have been developed in which the vector is deleted of essential genes and preparation of the vaccine is carried out in cell systems that provide the missing function.

A variety of vectors such as retroviral, lentiviral, herpes virus, poxvirus, adenoviral and adeno-associated viral vectors can be used for the delivery of heterologous genes to target cells. The heterologous gene of interest may be inserted into the viral vector. The viral vectors of the invention may comprise for example a virus vector provided with an origin of replication, optionally a promoter for the expression of the heterologous gene and optionally a regulator of the promoter. For example, adenoviruses useful in the practice of the present invention can have deletions in the E1 and/or E3 and/or E4 region, or can otherwise be maximized for receiving heterologous DNA.

The viral vector may comprise a constitutive promoter such as a cytomegalovirus (CMV) promoter, SV40 large T antigen promoter, mouse mammary tumour virus LTR promoter, adenovirus major late promoter (MLP), the mouse mammary tumour virus LTR promoter, the SV40 early promoter, adenovirus promoters such as the adenovirus major late promoter (Ad MLP), HSV promoters (such as the HSV IE promoters), HPV promoters such as the HPV upstream regulatory region (URR) or rous sarcoma virus promoter together with other viral nucleic acid sequences operably linked to the heterologous gene of interest. Tissue-specific or inducible promoters can also be used to control expression of the heterologous gene of interest. Promoters may also be selected to be compatible with the host cell for which expression is designed.

The viral vector may also comprise other transcriptional modulator elements such as enhancers. Enhancers are broadly defined as a cis-acting agent, which when operably linked to a promoter/gene sequence, will increase transcription of that gene sequence. Enhancers can function from positions that are much further away from a sequence of interest than other expression control elements (e.g. promoters) and may operate when positioned in either orientation relative to the sequence of interest. Enhancers have been identified from a number of viral sources, including polyoma virus, BK virus, cytomegalovirus (CMV), adenovirus, simian virus 40 (SV40), Moloney sarcoma virus, bovine papilloma virus and Rous sarcoma virus. Examples of suitable enhancers include the SV40 early gene enhancer, the enhancer/promoter derived from the long terminal repeat (LTR) of the Rous Sarcoma Virus, and elements derived from human or murine CMV, for example, elements included in the CMV intron A sequence.

The viral vector containing a heterologous gene of interest may then be preserved according to the method of the invention before storage, subjecting to further preservation techniques such as lyophilisation, or administration to a patient or host cell.

Nucleic acids encoding for polypeptides known to display antiviral activity, immunomodulatory molecules such as cytokines (e.g. TNF-alpha, interferons such as IL-6, and IL-2, interferons, colony stimulating factors such as GM-CSF), adjuvants and co-stimulatory and accessory molecules may be included in the viral vector of the invention. Alternatively, such polypeptides may be provided separately, for example in the preservation mixture of the invention or may be administrated simultaneously, sequentially or separately with viral vectors of the invention.

Preferably, the preserved viral vector of the invention may be introduced into suitable host cells using a variety of viral techniques that are known in the art, such as for example infection with recombinant viral vectors such as retroviruses, herpes simplex virus and adenoviruses. Preferably, administration of the preserved viral vector of the invention containing a gene of interest is mediated by viral infection of a target cell.

A number of viral based systems have been developed for transfecting mammalian cells.

For example, a selected recombinant nucleic acid molecule can be inserted into a vector and packaged as retroviral particles using techniques known in the art. The recombinant virus can then be isolated and delivered to cells of the subject either in vivo or ex vivo. Retroviral vectors may be based upon the Moloney murine leukaemia virus (Mo-MLV). In a retroviral vector, one or more of the viral genes (gag, pol & env) are generally replaced with the gene of interest.

A number of adenovirus vectors are known. Adenovirus subgroup C serotypes 2 and 5 are commonly used as vectors. The wild type adenovirus genome is approximately 35 kb of which up to 30 kb can be replaced with foreign DNA.

There are four early transcriptional units (E1, E2, E3 & E4), which have regulatory functions, and a late transcript, which codes for structural proteins. Adenovirus vectors may have the E1 and/or E3 gene inactivated. The missing gene(s) may then be supplied in trans either by a helper virus, plasmid or integrated into a helper cell genome. Adenovirus vectors may use an E2a temperature sensitive mutant or an E4 deletion. Minimal adenovirus vectors may contain only the inverted terminal repeats (ITRs) & a packaging sequence around the transgene, all the necessary viral genes being provided in trans by a helper virus. Suitable adenoviral vectors thus include Ad5 vectors and simian adenovirus vectors.

Viral vectors may also be derived from the pox family of viruses, including vaccinia viruses and avian poxvirus such as fowlpox vaccines. For example, modified vaccinia virus Ankara (MVA) is a strain of vaccinia virus which does not replicate in most cell types, including normal human tissues. A recombinant MVA vector may therefore be used to deliver the polypeptide of the invention.

Addition types of virus such as adeno-associated virus (AAV) and herpes simplex virus (HSV) may also be used to develop suitable vector systems Excipient In the present invention, an excipient for the preservation of viral particles is also provided. The excipient comprises (a) sucrose, stachyose, trehalose, a sugar alcohol or raffinose or any combination thereof; and (b) PEI at a concentration based on $M_n$ of 5M or less. By "excipient" is meant an inactive substance used as a carrier for the viral particles of the invention (for example when the viral particles are used as a vaccine). Typically, the viral particles (e.g. for use as a vaccine) are dissolved into or mixed with the excipient, which acts as a preservative of the viral particle and/or in some contexts aids administration and absorption into the body. As well as the preservation mixture of the present invention, an excipient may also comprise other preservatives such as antioxidants, lubricants and binders well known in the art, as long as those ingredients do not significantly reduce the effectiveness of the preservation mixture of the present invention.

Assaying on a Solid Support

Preserved viral particles stored on a solid support may be used for diagnostic purposes or to monitor a vaccination regime. For example, a patient sample such as bodily fluid (blood, urine, saliva, phlegm, gastric juices etc) may be preserved according to the methods described herein by drying an admixture comprising the patient sample and preservation mixture of the present invention onto a solid support. Preserved patient samples may then be tested for the presence of viral antigens/epitopes in the sample using anti-viral antibodies (for example using ELISA). Alternatively, viral particles of interest may be preserved according to the methods described herein by drying an admixture comprising the viral particles and preservation mixture of the present invention onto a solid support. Patient samples may be tested for the presence of anti-viral antibodies by contacting the patient sample with a solid support onto which the viral particles of interest are attached. The formation of antigen-antibody complexes can elicit a measurable signal. The presence and/or amount of viral particle antigen-antibody complexes in a sample may be used to indicate the presence of a viral infection or progress of a vaccination regime in a patient.

Administration

Preserved vaccines or viral particles according to the present invention may be administered, in some instances after reconstitution of a freeze-dried product, to a subject in vivo using a variety of known routes and techniques. For example, the preserved vaccines can be provided as an injectable solution, suspension or emulsion and administered via parenteral, subcutaneous, oral, epidermal, intradermal, intramuscular, interarterial, intraperitoneal, intravenous injection using a conventional needle and syringe, or using a liquid jet injection system. Preserved vaccines may be administered topically to skin or mucosal tissue, such as nasally, intratracheally, intestinal, sublingually, rectally or vaginally, or provided as a finely divided spray suitable for respiratory or pulmonary administration.

In one embodiment, the method of the invention further comprises the step of processing the mixture into a formulation suitable for administration as a liquid injection. Preferably, the method further comprises the step of processing the mixture into a formulation suitable for administration via ingestion or via the pulmonary route.

The preserved product is administered to a subject in an amount that is compatible with the dosage formulation and that will be prophylactically and/or therapeutically effective. The administration of the preserved product or vaccine of the invention may be for either "prophylactic" or "therapeutic" purpose. As used herein, the term "therapeutic" or "treatment" includes any of the following: the prevention of infection or reinfection; the reduction or elimination of symptoms; and the reduction or complete elimination of a pathogen. Treatment may be effected prophylactically (prior to infection) or therapeutically (following infection).

The following Examples illustrate the invention. The PEI used in Example 1, 2, 3, 4, 5, 6, 7, 8 and 10 had an $M_w$ of 750000 and an $M_n$ of 60000 (Sigma P3143). The "high molecular weight" PEI used in Example 9 had a $M_w$ of 750000 and an $M_n$ of 60000 (Sigma P3143). The "low molecular weight" PEI of Example 9 had a $M_w$ of 1300 and an $M_n$ of 1200 (Aldrich 482595). The histone used in the Examples was histone 2A obtained from Boehringer Mannheim.

The following general experimental techniques were employed:

Freeze Drying

After vortexing, vials were frozen at −80° C. in freeze dryer trays containing 30 ml water with rubber stoppers partially in. Frozen vials were transferred to the freeze dryer stoppering shelf (Thermo Fisher) of the pre-cooled freeze dryer (Thermo Fisher) and dried for 16 hours. Rubber stoppers were lowered fully into the vials under a vacuum before removing from freeze dryer.

FMDV Assay

Virus and cells were cultivated in Dulbecco's modified Eagles medium (DMEM), supplemented with 10% foetal bovine serum, 20 mM glutamine, penicillin (100 U/ml) and streptomycin (100 μg/ml). Eagles overlay medium was prepared by adding 25 ml indubiose dissolved in water (24 mg/ml) to 75 ml Eagles overlay, 5 ml tryptone phosphate broth, 1 ml foetal bovine serum (FBS) and 1 ml penicillin (100 U/ml) and streptomycin (100 μg/ml).

BHK-21 cells were prepared in 6-well tissue culture plates and grown overnight at 37° C. until approximately 80-90% confluent. Freeze-dried samples were re-suspended in DMEM. Cell monolayers were washed with Phosphate Buffered Saline (PBS) and incubated with 100 μl of FMDV sample at 37° C. for 15 minutes. Cell monolayers were overlaid with 2 ml of Eagles overlay which was allowed to set at room temperature (RT) before incubating at 37° C. for a further 40-48 hours.

Infected cell monolayers were stained with 2 ml methylene blue (4% formaldehyde in PBS) for 24 hours at RT and visualised plaques recorded.

Adenovirus Assay 96 flat bottomed cell culture dishes (Jencons, UK) were seeded with HEK 293 cells at $10^5$ cells per ml (100 μl per well) and maintained at 37° C. with 5% $CO_2$. After achieving 90% confluence vials containing the adenovirus plus excipient were reconstituted in 1 ml of DMEM plus 5% FBS. A 1:10 dilution step was then taken by taking 100 ml from the reconstituted vial and adding to 900 ml of DMEM. 100 ml of the resulting diluted virus was then added to the first row on the plate and a 1:2 dilution carried out down the plate. The process was then repeated with the next excipient. After a further 48 hours, the number GFP cells per well were counted using fluorescent microscopy.

Statistical Analysis

A student T-test was performed to analyse significance between different excipients using PRISM Graphpad software version 4.00. Alternatively, where multiple comparisons of pairs were necessary, a one way ANOVA was carried out with as Turkey post comparison test. The P value summaries are *$p<0.10$; $p<0.05$; and *$p<0.005$.

EXAMPLE 1

A recombinant adenovirus expressing enhanced green fluorescent protein (EGFP) with a titre of $4.1\times10^7$ pfu/ml (per ml tissue culture medium) was mixed (1:5 v/v) with an excipient comprising sucrose (a saturated solution, approximately 64% w/v), stachyose (a saturated solution, approximately 64% w/v) and PEI (33 μg/ml) at a ratio of 3:1:1 v/v respectively. The mixture was freeze-dried as follows: samples were frozen in liquid nitrogen, and dried under vacuum at room temperature for 16 hours. After this time samples were stored until use at −20° C. or used immediately. Adenovirus was assayed using a plaque assay in 293A cells. The results are shown in the following Table.

| Treatment | Titre (pfu/ml) |
| --- | --- |
| Pre-drying | $4.8 \times 10^7$ |
| Immediately post-drying | $4.3 \times 10^7$ |
| Post drying and 5 days at 37° C. | $4.1 \times 10^7$ |

EXAMPLE 2

This experiment was designed to examine the effect of excipient components on recovery of FMDV-A when freeze-dried (FD) and left for 24 hours at room temperature (RT) or heat treated for 48 hours at 37° C. (HT). All excipients were prepared in glass vials. All vials were set up in duplicate.

170 μl of an aqueous solution of Suc (1 g/ml) and 30 μl of an aqueous solution of Raf (1 g/ml) were added to each other, giving a total 200 μl volume for the sugar mix. 50 μl of PEI (0.03 mg/ml) was then added to complete the excipient. Finally, 50 μl of FMDV-A were added and the mixture vortexed. The final concentration of each sugar and of PEI in the excipient mixture is shown in the Table below:

| Excipient Component | Final Concentration in Excipient |
| --- | --- |
| Sucrose | 1.7 (M) |
| Raffinose | 0.1 (M) |
| PEI | 6.25 (nM)*/78.13 (nM)[1] |

*concentration calculated from $M_w$
[1]concentration calculated from $M_n$

A control mixture was prepared by addition of 50 μl of FMDV-A to 250 μl of PBS. The vials were freeze-dried and then left at RT for 24 hours or 37° C. for 48 hours. An FMDV assay was then performed. The results are shown in FIG. 1. The results demonstrate that there is very little virus recovery when the excipient was PBS only. The excipient containing Suc, Raf and PEI demonstrated similar FMDV recovery at RT or HT. A student T-test in fact showed no significant difference between incubation at room temperature (RT) and heat treating for 48 hours at 37° C. (HT).

EXAMPLE 3

This experiment was designed to investigate the benefit of PEI on heat treated FMDV-O virus. Glass vials were prepared in duplicate with 120 μl Suc (3M), 80 μl Stac (0.75M) and 50 μl of either PEI ($10^{-2}$ mg/ml) or distilled water. 50 μl FMDV-O was added to each excipient vial. The final concentration of each sugar and of PEI, when present, in the excipient mixture is shown in the Table below:

| Excipient Component | Final Concentration in Excipient |
| --- | --- |
| Sucrose | 1.2 (M) |
| Stachyose | 0.2 (M) |
| PEI | 2 (nM)*/25 (nM)[1] |

*concentration calculated from $M_w$
[1]concentration calculated from $M_n$

Figure 2:
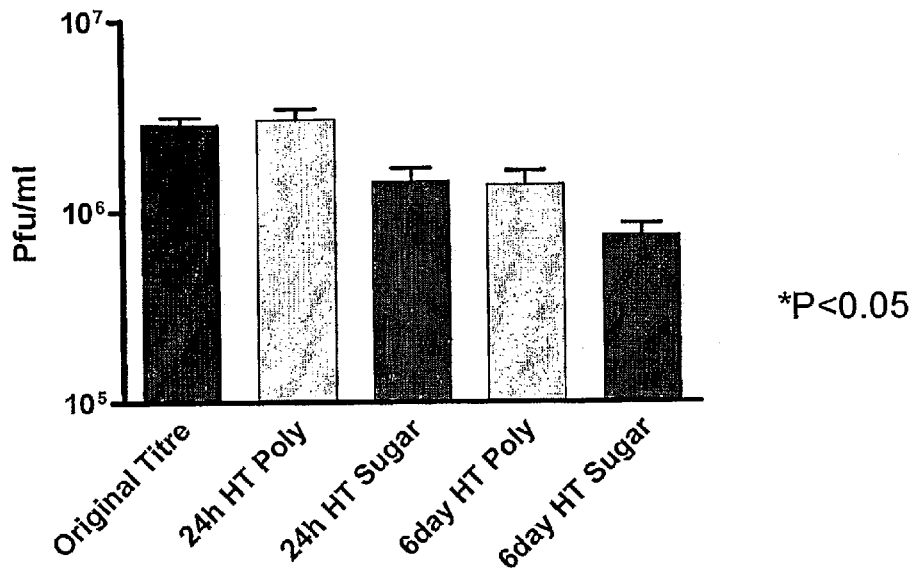
FIG. 2 shows that PEI enhances the recovery of FMDV-O when added to the sugars sucrose (Suc) and stachyose (Stac). The results obtained by use of an excipient containing PEI, Suc and Stac are denoted by "Poly". The results obtained by use of an excipient containing Suc and Stac without PEI are denoted by "Sugar". The effect is seen with FMDV-O heat treated for both 24 hours ("24 h HT") and 6 days ("6 day HT"). Error bars shown are standard error of the mean (n=2).

50 μl Volumes of the virus used were also refrozen as controls (original titre). After freeze-drying, samples were incubated at 37° C. for either 24 hours or 6 days. Samples were re-suspended in 1 ml DMEM (plus 10% FBS) and virus recovery determined in the plaque assay. The results are shown in FIG. 2.

Example 3 was designed to assess the extra benefit of including PEI in the sugar excipient over simply having the sugar excipient alone. Following heat treatment at 37° C. for 24 hours, there was no noticeable drop in virus recovery when the excipient containing PEI was used whereas the recovery of virus was significantly reduced when the sugar excipient was employed without PEI. After 6 days of heat treatment, there was a loss of virus when the excipient containing PEI was used. However, again, this loss was significantly lower than the loss when the excipient containing sugar alone was employed.

EXAMPLE 4

Initial sugar concentrations were examined to optimise the excipient sugar component in the recovery of FMDV-O. A sugar solution with a 120:80 Suc (3M) and Stac (0.75M) ratio was prepared ("sugars") and 1:10, 1:100, 1:1000 serial dilutions carried out. Triplicate glass vials with 200 µl of each sugar concentration or PBS were prepared and 50 µl FMDV-O added to the sugar solution or PBS.

The final concentration of each sugar is shown in the Table below:

| Excipient Component | Final Concentration in Excipient |
|---|---|
| Sucrose | 1.2 (M) |
| Sucrose 1:10 | 0.12 (M) |
| Sucrose 1:100 | 0.012 (M) |
| Sucrose 1:1000 | 0.0012 (M) |
| Stachyose | 0.2 (M) |
| Stachyose 1:10 | 0.02 (M) |
| Stachyose 1:100 | 0.002 (M) |
| Stachyose 1:1000 | 0.0002 (M) |

Figure 3:
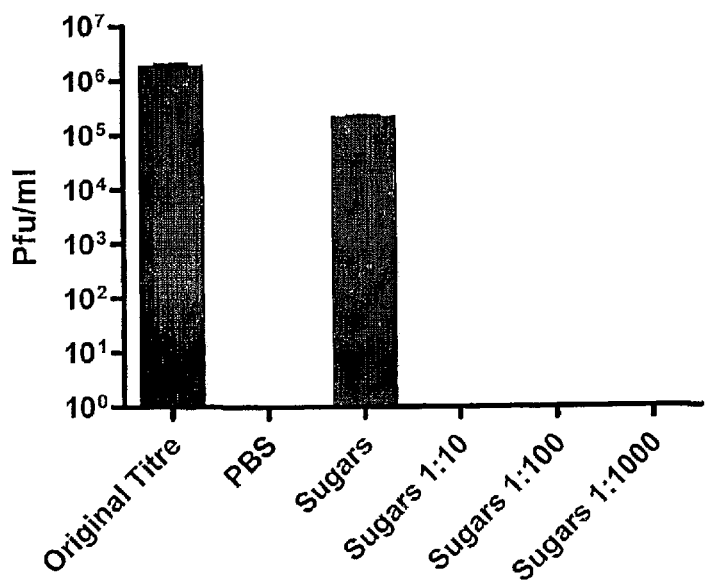
FIG. 3 shows that the initial sugar concentration in the excipient is important in maintaining FMDV-O stability. Diluting a solution of sucrose and stachyose (120 Suc (3M): 80 Stac (0.75M)) 1:10 by volume produces a complete loss in the protective effects of a sugar only excipient. Error bars shown are standard error of the mean (n=3).

50 µl volumes of the virus were also refrozen as controls (original titre). Samples were freeze-dried, then incubated at 37° C. for 7 days before re-suspension in 1 ml DMEM (plus 10% FBS) and virus recovery determined in the plaque assay. The results are shown in FIG. 3.

The aim of Example 4 was to see the effect of diluting sugar concentration. Following freeze drying, virus recovery drops to approximately one tenth of the original titre in an excipient containing the sugar solution. When the sugar concentration is diluted 1:10, no significant recovery is seen.

EXAMPLE 5

Example 5 was designed to investigate the effect of optimal combinations of sucrose and stachyose concentrations for recovery of FMDV-O. A series of sugar ratios from 80 µl Suc (3M) and 120 µl Stac (0.75M) to 200 µl Suc and 1 µl Stac were prepared. PEI was prepared with a series of dilutions of 1 mg/ml from 1:100 to 1:32000. His was prepared with a series of dilutions from 1 mg/ml to 0.625 mg/ml. A matrix of samples was prepared with 50 µl FMDV-O, 200 µl of each sugar ratio and 50 µl each PEI dilution.

The final concentration of each sugar and of PEI is shown in the Table below:

| Excipient Component | Final Concentration in Excipient |
|---|---|
| Sucrose 80 µl | 0.8 (M) |
| Sucrose 100 µl | 1 (M) |
| Sucrose 120 µl | 1.2 (M) |
| Sucrose 140 µl | 1.4 (M) |
| Sucrose 160 µl | 1.6 (M) |
| Sucrose 180 µl | 1.8 (M) |
| Sucrose 200 µl | 2 (M) |
| Stachyose 120 µl | 0.3 (M) |
| Stachyose 100 µl | 0.25 (M) |
| Stachyose 80 µl | 0.2 (M) |
| Stachyose 60 µl | 0.15 (M) |
| Stacyose 40 µl | 0.1 (M) |
| Stachyose 20 µl | 0.05 (M) |
| PEI 1:100 mg/ml-1:32000 mg/ml | 2-0.006 (nM)*/25-0.075 (nM)[1] |
| Histone 1 mg/ml-0.0625 mg/ml | 0.17-0.01 mg/ml |

*concentration calculated from $M_w$
[1]concentration calculated from $M_n$

Samples were freeze-dried and incubated at 37° C. for 3 days (PEI samples) or 24 hours (His samples) before re-suspending in 1 ml DMEM plus 10% FBS) and determining FMDV recovery in the plaque assay. The results are shown in FIGS. 4.1 and 4.2.

The results for each PEI concentration were collated. The results shown in FIG. 4.1 demonstrate that a significantly lower recovery was seen when using a sucrose only excipient compared to an excipient containing a 140:60 ratio of Suc: Stac. Apart from a pure Suc excipient there was no significant difference between the different ratios of Suc:Stac.

FIG. 4.2 shows the results of the same experiment in which His is replaced with PEI in the excipient. The results demonstrated an effect on optimal Suc:Stac ratios with far higher ratios of Suc being preferable and no noticeable deleterious of a Suc only excipient.

EXAMPLE 6

In this Example, adenovirus with a GFP tag was used to compare virus recovery with different sugar/PEI concentrations. A series of different Suc:Stac ratios were set up with a final volume of 200 µl. 50 µl of PEI at a range of concentrations from 0.1 mg per ml to 0.01 µg per ml were also added to each vial. After addition of adenovirus to the different Suc:Stac:PEI ratios, vials were frozen and FD.

The final concentration of each sugar and of PEI is shown in the Table below:

| Excipient Component | Final Concentration in Excipient |
|---|---|
| Sucrose 200 µl | 2 (M) |
| Sucrose 160 µl | 1.6 (M) |
| Sucrose 120 µl | 1.2 (M) |
| Sucrose 80 µl | 0.8 (M) |
| Sucrose 40 µl | 0.4 (M) |
| Stachyose 40 µl | 0.1 (M) |
| Stachyose 80 µl | 0.2(M) |
| Stachyose 120 µl | 0.3 (M) |
| Stachyose 160 µl | 0.4 (M) |
| Stachyose 200 µl | 0.5 (M) |
| PEI 1:10 mg/ml | 20 (nM)*/250 (nM)[1] |
| PEI 1:50 mg/ml | 4 (nM)*/50 (nM)[1] |
| PEI 1:1000 mg/ml | 0.2 (M)*/2.5 (nM)[1] |
| PEI 1:10000 mg/ml | 0.02 (nM)*/0.25 (nM) [1] |

*concentration calculated from $M_w$
[1]concentration calculated from $M_n$

Figure 5:
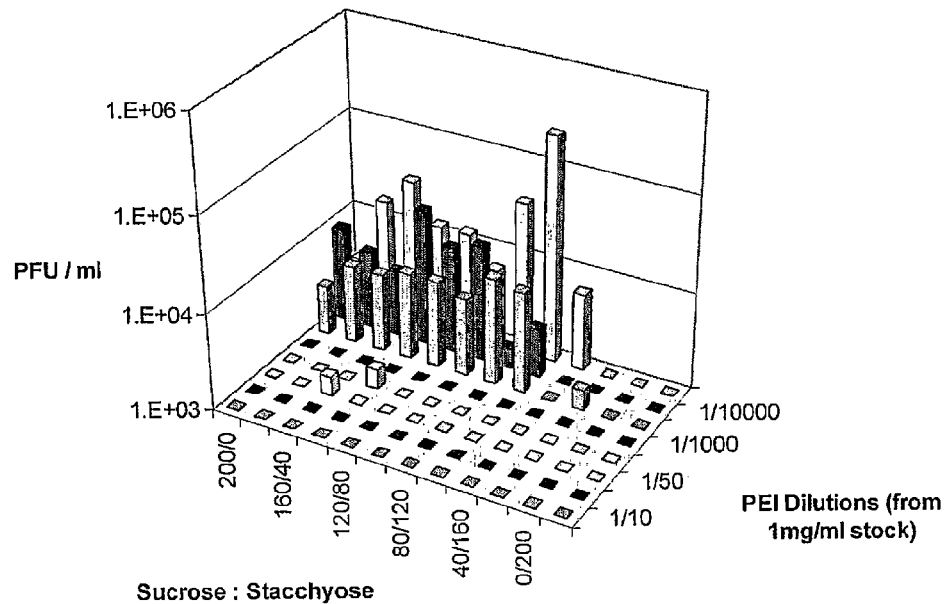

Following 24 hours of heat treatment at 37° C., excipient and virus were reconstituted in 1 ml of DMEM (plus 10% FBS). Virus titre was assayed using 2 fold serial dilutions in 96 well plates containing a 90% confluent monolayer of 293 cells. The results are shown in FIG. 5.

Initial optimisation examined three variables: Suc concentration, Stac concentration and PEI concentration using a matrix of different concentrations. The results of the matrix demonstrate that both sugar concentration and PEI concentration can pronouncedly effect viral recovery. High concentrations of Stac to Suc or high concentrations of PEI both showed low levels of recovery. Optimal recovery of virus required Suc to be present. Samples containing no Sue showed no recovery.

EXAMPLE 7

The aim of this experiment was to examine PEI concentration in a Suc:Stac sugar excipient. A series of 1:10 dilutions of PEI were set up to assess optimal PEI concentrations. From the work on optimising sugar concentrations, a ratio of 120:80 Suc:Stac was chosen.

The final concentration of each sugar and of PEI is shown in the Table below:

| Excipient Component | Final Concentration in Excipient |
|---|---|
| Sucrose | 0.8 (M) |
| Stachyose | 0.2 (M) |
| PEI 100 µg/ml | 20 (nM)*/250 (nM)[1] |
| PEI 10 µg/ml | 2 (nM)*/25 (nM)[1] |
| PEI 1 µg/ml | 0.2 (nM)*/2.5 (nM)[1] |
| PEI 0.1 µg/ml | 0.02 (nM)*/0.25 (nM)[1] |
| PEI 0.01 µg/ml | 0.002 (nM)*/0.025 (nM)[1] |
| PEI 0.001 µg/ml | 0.0002 (nM)*/0.0025 (nM)[1] |

*concentration calculated from $M_w$
[1]concentration calculated from $M_n$

Figure 6:
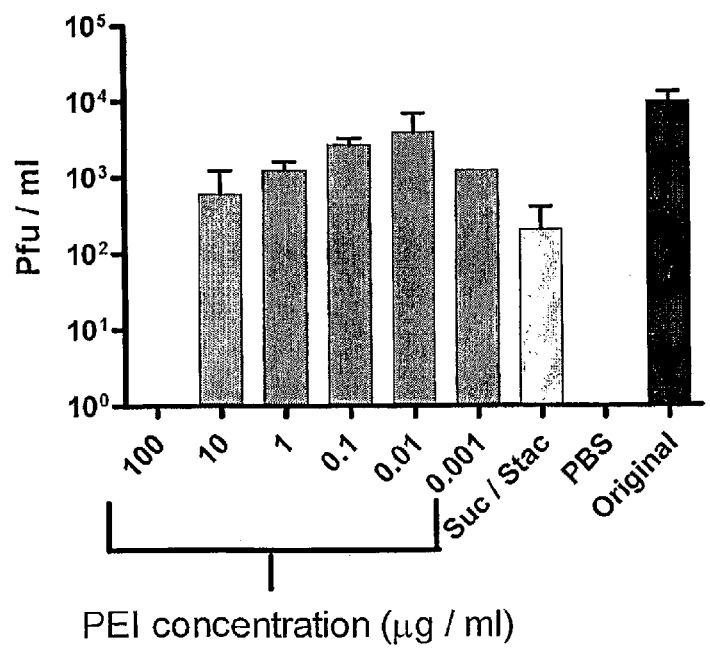

Following freeze drying, samples were heat treated at 37° C. for 24 hours then the adenovirus assay was carried out. The results are shown in FIG. 6.

The results demonstrate that when PEI is used at the higher concentrations low virus recovery is seen. As PEI is further diluted, virus recovery improves with an optimal concentration of around 0.01 µg/ml. The recovery at this concentration was significantly higher than virus recovery using sugar excipients only. Excipient containing PBS showed no virus recovery.

EXAMPLE 8

This experiment was designed to gain a greater understanding of the different excipient components on virus stability during freeze drying.

The final concentration of each sugar and of PEI is shown in the Table below:

| Excipient | Final Concentration before freeze drying |
|---|---|
| Sucrose | 1.5M |
| Stachyose | 0.125M |
| PEI (10-2) | 2 nM*/25 nM[1] |
| PEI (10-4) | 0.02 nM*/0.25 nM[1] |

*concentration calculated from $M_w$
[1]concentratin calculated from $M_n$

Figure 7:
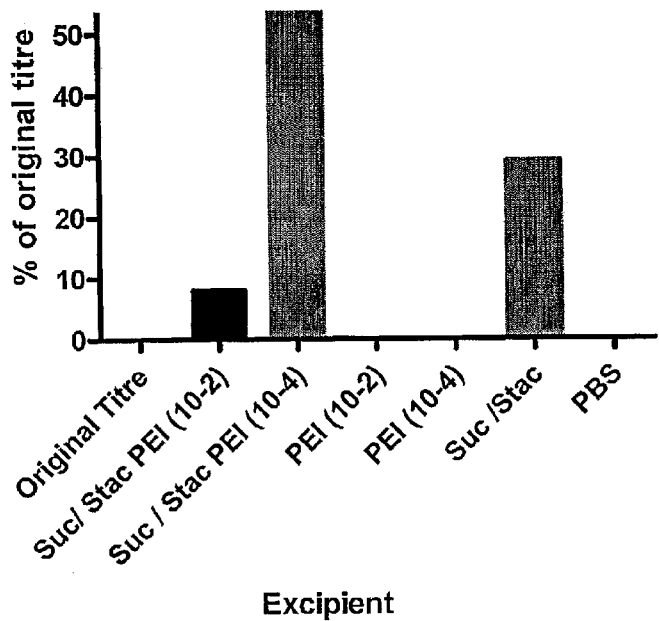

Vials containing excipient plus virus were freeze dried over night. Following freeze drying, vials were incubated at 37° C. for 5 days prior to re-suspending in 1 ml of DMEM (10% FBS). The resulting solution was then diluted 1:1000 before carrying out a series of 1:2 dilutions prior to proceeding to the 293 assay. The results are shown in FIG. 7.

EXAMPLE 9

Example 9 was designed to study the differences between high and low molecular weight PEI. The high molecular weight PEI ("HPEI") has a $M_w$ of 750000 whereas the low molecular weight PEI ("LPEI") has a $M_w$ of 1300.

The final concentration of each sugar and of PEI is shown in the Table below:

| Excipient | Final Concentration before freeze drying |
|---|---|
| Sucrose | 1.5M |
| Stachyose | 0.125M |
| HPEI (10-2) | 2 nM*/25 nM[1] |
| HPEI (10-3) | 0.2 nM*/2.5 nM[1] |
| HPEI (10-4) | 0.02 nM*/0.25 nM[1] |
| HPEI (10-5) | 0.002 nM*/0.025 nM[1] |
| LPEI (10-2) | 1.28 µM*/1.38 µM[1] |
| LPEI (10-3) | 0.128 µM*/0.138 µM[1] |
| LPEI (10-4) | 0.0128 µM*/0.0138 µM[1] |
| LPEI (10-5) | 0.00128 µM*/0.00138 µM[1] |

*concentration calculated at $M_w$
[1]concentration calculated at $M_n$

Figure 8:
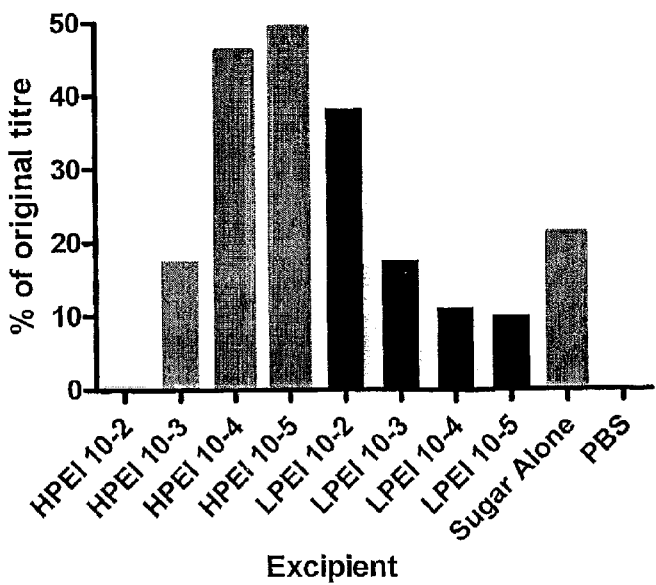

Vials containing excipient plus adenovirus were freeze dried over night. Following freeze drying, vials were incubated at 37° C. for 5 days prior to re-suspending in 1 ml of DMEM (10% FBS). The resulting solution was then diluted 1:1000 before carrying out a series of 1:2 dilutions prior to proceeding to the 293 assay. The results are shown in FIG. 8.

EXAMPLE 10

Example 10 was designed to examine the differences in adenovirus recovery when PEI (high molecular weight; $M_w$ 750000) was diluted in PBS ("PEIP") or water ("PEIW").

The final concentration of each sugar and of PEI is shown in the Table below:

| Excipient | Final Concentration before freeze drying |
|---|---|
| Sucrose | 1.5M |
| Stachyose | 0.125M |
| PEI (10-2) | 2 nM*/25 nM[1] |
| PEI (10-3) | 0.2 nM*/2.5 nM[1] |
| PEI (10-4) | 0.02 nM*/0.25 nM[1] |
| PEI (10-5) | 0.002 nM*/0.025 nM[1] |

*concentration calculated from $M_w$
[1]concentration calculated from $M_n$

Figure 9:
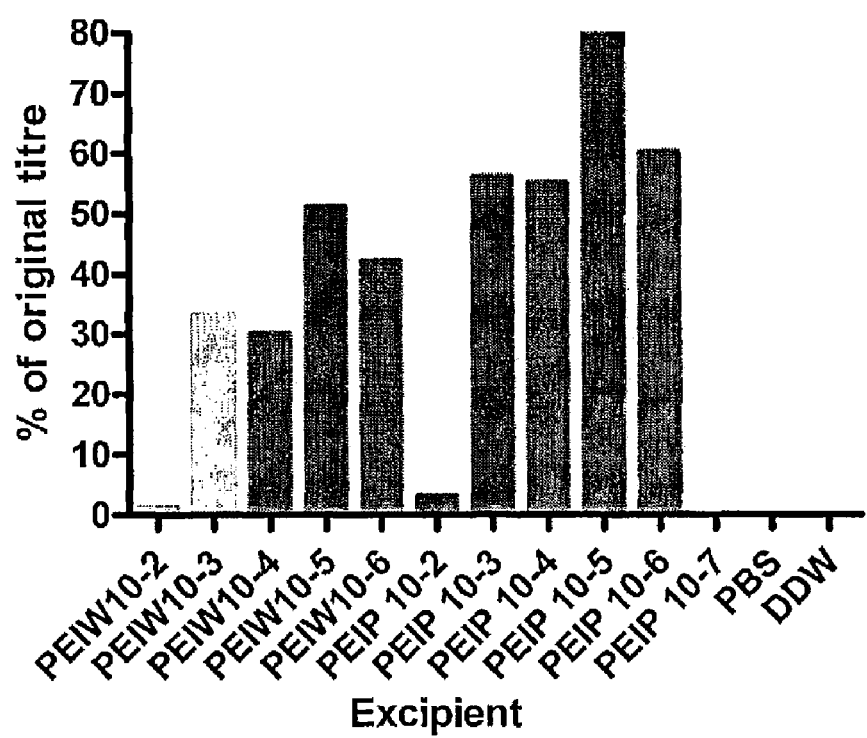

Vials containing excipient plus virus were freeze dried over night. Following freeze drying, vials were incubated at 37° C. for 5 days prior to re-suspending in 1 ml of DMEM (10% FBS). The resulting solution was then diluted 1:1000 before carrying out a series of 1:2 dilutions prior to proceeding to the 293 assay. The results are shown in FIG. 9.

The invention claimed is:

1. A method for preserving viral particles comprising:
   (i) providing an aqueous solution of one or more sugars, a polyethyleneimine and said viral particles wherein, (a) the concentration of polyethyleneimine is less than 5 nM based on the number-average molar mass ($M_n$) of the polyethyleneimine, and (b) said aqueous solution comprises sucrose at a concentration of 0.8M or greater; and
   (ii) freeze-drying the solution to form an amorphous solid matrix comprising said viral particles.

2. The method according to claim 1, wherein the concentration of polyethyleneimine is between 0.0025 and 5 nM, based on the number-average molar mass ($M_n$) of the polyethyleneimine.

3. The method according to claim 1, wherein the concentration of polyethyleneimine is between 0.025 and 2.5 nM, based on the number-average molar mass ($M_n$) of the polyethyleneimine.

4. The method according to claim 1, in which the $M_n$ of the polyethyleneimine is between 20 and 1000 kDa and the concentration of the polyethyleneimine is between 0.001 and 5 nM based on the $M_n$.

5. The method according to claim 1, wherein the $M_n$ of the polyethyleneimine is between 300 and 2000 Da.

6. The method according to claim 1, in which the sugar concentration, or total sugar concentration, is between 0.8M and 2M.

7. The method according to claim 1, wherein said aqueous solution further comprises stachyose, raffinose or a sugar alcohol.

8. The method according to claim 1, wherein said aqueous solution comprises one or more additional sugars.

9. The method according to claim 8, wherein the concentration of sucrose relative to another sugar is at a ratio of between 3:7 and 9:1; and the concentration of polyethyleneimine based on $M_n$ in step (i) is between 0.0025 nM and 5 nM.

10. The method according to claim 1, in which the viral particles are composed of a live virus or killed virus.

11. The method according to claim 10, in which the live virus is whole virus or live-attenuated virus.

12. A method of preparing a composition comprising viral particles, which method comprises:
    (a) providing an aqueous solution of one or more sugars, a polyethyleneimine and said viral particles, wherein (i) the concentration of polyethyleneimine is less than 5 nM based on the number-average molar mass ($M_n$) of the polyethyleneimine, and (ii) said aqueous solution comprises sucrose at a concentration of 0.8M or greater;
    (b) adding an adjuvant, buffer, antibiotic and/or additive to the admixture; and
    (c) freeze-drying the solution to form an amorphous solid matrix comprising said viral particles.

13. The method according to claim 12, wherein said composition comprises two or more different types of viral particles.

* * * * *